United States Patent
Hu et al.

(10) Patent No.: US 7,138,229 B2
(45) Date of Patent: Nov. 21, 2006

(54) SYSTEMS AND METHODS FOR CHARACTERIZING KIDNEY DISEASES

(75) Inventors: Huaizhong Hu, Madison, WI (US); Stuart Knechtle, Fitchburg, WI (US)

(73) Assignee: Renovar, Inc., Madison ( * ) Notice: Subject to any disclaimer, the term of this patent is extended or adjusted under 35 U.S.C. 154(b) by 58 days.

(21) Appl. No.: 10/903,797

(22) Filed: Jul. 30, 2004

(65) Prior Publication Data

US 2005/0112688 A1    May 26, 2005

Related U.S. Application Data

(63) Continuation-in-part of application No. 10/313,807, filed on Dec. 6, 2002.

(60) Provisional application No. 60/499,937, filed on Sep. 3, 2003, provisional application No. 60/491,900, filed on Aug. 1, 2003.

(51) Int. Cl.
*C12Q 1/00* (2006.01)

(52) U.S. Cl. .......................................................... 435/4

(58) Field of Classification Search .................. 435/7.1, 435/4, 975
See application file for complete search history.

(56) References Cited

OTHER PUBLICATIONS

Romagnani et al, J. Am. Soc. Nephrology, vol. 10, pp. 2518-2526, (1999).*
Loetscher et al, J. Exp. Med., vol. 184, pp. 963-969, (Sep. 1996).*

* cited by examiner

*Primary Examiner*—Christopher R. Tate
*Assistant Examiner*—Amanda P. Wood
(74) *Attorney, Agent, or Firm*—Medlen & Carroll, LLP (57) ABSTRACT

The present invention relates to methods of diagnosing, predicting and monitoring kidney diseases, including acute renal failure, renal tubular interstitial disease and glomerulonephritis. In particular, the present invention relates to the detection, prediction and monitoring of kidney diseases by detection of CXCR3 and CCL chemokines in urine. The present invention further relates to methods and compositions for assessing the efficacy of agents and interventions used to treat kidney diseases.

20 Claims, 6 Drawing Sheets

|  | acute rejection (n=28) | suspicious acute rejection (n=9) | BK virus nephritis (n=6) | acute tubular injury (n=10) | chronic rejection (n=20) | stable graft function (n=26) | healthy control (n=16) |
|---|---|---|---|---|---|---|---|
| IP-10 | 25 (89.3%) | 4 (44.4%) | 6 (100%) | 7 (70.0%) | 2 (10.0%) | 2 (7.6%) | 0 (0%) |
| Mig | 21 (75%) | 3 (33.3%) | 6 (100%) | 8 (80.0%) | 2 (10.0%) | 1 (3.8%) | 0 (0%) |
| I-TAC | 10 (35.7%) | 0 (0%) | 2 (33.3%) | 3 (30.0%) | 0 (0%) | 0 (0%) | 0 (0%) |
| IP-10+Mig | 25 (89.3%) | 4 (44.4%) | 6 (100%) | 8 (80.0%) | 4 (20.0%) | 2 (7.6%) | 0 (0%) |

Figure 4.

|  | Sensitivity (%) | Specificity (%) | Positive predictive value (%) | Negative predictive value (%) |
|---|---|---|---|---|
| IP-10 | 86.4 | 91.3 | 90.5 | 87.5 |
| Mig | 79.5 | 93.5 | 92.1 | 82.7 |
| IP-10 and Mig | 88.6 | 87.0 | 86.6 | 88.9 |

Day after diagnosis of acute rejection

SYSTEMS AND METHODS FOR CHARACTERIZING KIDNEY DISEASES

The present application is a continuation-in-part of U.S. application Ser. No. 10/313,807, filed Dec. 6, 2002, which is incorporated herein by reference in its entirety. The present application also claims priority from U.S. provisional patent application Ser. Nos. 60/491,900, filed Aug. 1, 2003 and 60/499,937, filed Sep. 3, 2003, each of which is herein incorporated by reference in its entirety.

FIELD OF THE INVENTION

The present invention relates to methods of diagnosing, predicting and monitoring kidney diseases, including acute renal failure, renal tubular interstitial disease and glomerulonephritis. In particular, the present invention relates to the detection, prediction and monitoring of kidney diseases by detection of CXCR3 and CCL chemokines in urine. The present invention further relates to methods and compositions for assessing the efficacy of agents and interventions used to treat kidney diseases.

BACKGROUND OF THE INVENTION

The diagnosis of acute renal failure, tubular interstitial disease, renal cancer or glomerulonephritis is classically based on the presence of one or more symptoms. For example, symptoms of acute renal failure, renal tubular injury, renal cancer or glomerulonephritis may include weight gain, reduced urine output, increased serum creatine concentrations, hypertension, fever, and kidney enlargement and tenderness. However, the use of these symptoms alone to detect renal failure is not adequate. Currently, most episodes of renal failure are diagnosed by measuring kidney function, for example by using biochemical tests such as assays that measure serum creatinine (Cr) concentrations, and by imaging or biopsy.

Presently, renal biopsy remains the most definitive test to specifically diagnose acute renal failure, tubular interstitial disease, renal cancer or glomerulonephritis. However, this method has major limitations. For example, the biopsy procedure itself has complications, and cannot be performed on a routine or even frequent basis to monitor progression of renal disease. In addition, the invasive nature of a renal biopsy is both uncomfortable and inconvenient for patient subjects. Accurate interpretation of the renal biopsy also demands the expertise of a pathologist with extensive experience in analyzing a biopsy sample for evidence of acute renal failure, tubular interstitial disease, renal cancer or glomerulonephritis. Hence, renal biopsies are reserved for those patients that demonstrate other clinical and/or laboratory evidence of renal failure, thus limiting its use or potential use in detecting early disease.

A method for the early detection and/or prediction of acute renal failure, tubular intersitial disease, renal cancer or glomerulonephritis would thus be an important clinical tool for diagnosing and monitoring renal disease.

SUMMARY OF THE INVENTION

The present invention relates to methods of diagnosing and predicting kidney disease, including acute renal failure, renal tubular interstitial disease, renal cancer and glomerulonephritis. In particular, the present invention relates to the detection, prediction and monitoring of kidney diseases by detection of CXCR3 and CCL chemokines in urine, or other body fluids, for example, blood, serum, plasma, bile, saliva, or cerebrospinal fluid.

Accordingly, in some embodiments, the present invention provides a method of detecting kidney disease markers, comprising providing a urine sample from a subject, wherein said subject is suspected of having acute renal failure, renal tubular interstitial disease or glomerulonephritis; reagents for detection of a CXCR3 ligand or CCR-5 receptor ligand (e.g., CCL chemokines); and detecting the presence of said ligand in said urine sample using said reagents. In some embodiments, the method further provides the step of predicting renal failure risk in the subject based on the result of the detecting. In other embodiments, the method further provides the step of detecting renal failure risk in the subject based on the result of the detecting. In some embodiments, detecting the presence of the ligand in the urine sample comprises detecting the amount of the ligand in the urine sample. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full length ligand. In other embodiments, the ligand is a fragment of the full length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the present invention further comprises the step of determining a treatment course of action based on the prediction of acute renal failure, tubular interstitial disease or glomerulonephritis risk. In some embodiments, the treatment course of action comprises the administration of therapeutic agents. In some embodiments, the treatment course of action comprises a surgical procedure. In additional embodiments the surgical procedure comprises renal transplantation. In further embodiments the treatment course of action comprises dialysis. In some embodiments the dialysis is hemodialysis. In other embodiments the dialysis is peritoneal dialysis. In other embodiments, the treatment course of action comprises continued monitoring. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

The present invention further provides a method of diagnosing acute renal failure, tubular interstitial disease, renal cancer or glomerulonephritis in a subject, comprising providing a urine sample from a subject; reagents for detection of a CXCR3 ligand or CCR-5 receptor ligand (e.g., CCL chemokines); and detecting the presence of the ligand in the urine sample using the reagents; and diagnosing acute renal failure, tubular interstitial disease, renal cancer or glomerulonephritis in the subject based on the result of the detecting. In some embodiments, detecting the presence of the ligand in the urine sample comprises detecting the amount of the ligand in the urine sample. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full-length ligand. In other embodiments, the ligand is a fragment of the full length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the method further comprises the step of determining a treatment course of action based on the diagnosis of acute renal failure, tubular interstitial disease or glomerulonephritis. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

The present invention additionally provides a method of determining a treatment course of action, comprising providing a urine sample from a subject, wherein the subject is suspected of having acute renal failure, tubular interstitial disease, renal cancer or glomerulonephritis for detection of a chemokine; and detecting the amount of the chemokine in the urine sample using the reagents; and determining a treatment course of action based on the detecting. In some embodiments, the treatment course of action comprises continued monitoring. In some embodiments, the chemokine comprises a CXCR3 ligand or a CCL chemokine. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full-length ligand. In other embodiments, the ligand is a fragment of a full-length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the present invention further comprises the step of determining a treatment course of action based on the prediction of acute renal failure, tubular interstitial disease or glomerulonephritis risk. In some embodiments, the treatment course of action comprises the administration of therapeutic agents. In some embodiments, the treatment course of action comprises a surgical procedure. In additional embodiments the surgical procedure comprises renal transplantation. In further embodiments the treatment course of action comprises dialysis. In some embodiments the dialysis is hemodialysis. In other embodiments the dialysis is peritoneal dialysis. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

The present invention also provides a method of screening compounds, comprising providing a sample from a subject, wherein the subject is suspected of having acute renal failure, tubular interstitial disease or glomerulonephritis; an assay with reagents for detection of a CXCR3 ligand or CCR-5 receptor ligand (e.g., CCL chemokines); and one or more test compounds; and administering the test compound to the subject; detecting the amount of the ligand in the sample using the reagents. The present invention is not limited to a particular sample type. Any bodily fluid including, but not limited to, blood, urine, serum, and lymph may be utilized. In some preferred embodiments, the sample is a urine sample. In some embodiments, the test compound is a drug. In some embodiments, the method further comprises the step of determining the efficacy of the drug based on the detecting. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full-length ligand. In other embodiments, the ligand is a fragment of a full-length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

In still further embodiments, the present invention provides a kit, comprising reagents for the detection of the amount of a CXCR3 ligand or CCR-5 receptor ligand (e.g., CCL chemokines) in a urine sample from a subject suspected of having acute renal failure, renal tubular interstitial disease or glomerulonephritis, and instructions for using the reagents for detecting the presence of the ligand in the urine sample. The present invention is not limited to the detection of a particular ligand. Any suitable ligand is contemplated including, but not limited to, IP-10, Mig, I-TAC, MIP-1α, MIP-3α, and MIP-1β. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the instructions comprise instructions required by the United States Food and Drug Administration for use in in vitro diagnostic products. In some embodiments, the kit further comprises second reagents for determining the presence or absence of a concurrent infection in the subject and second instructions for using the reagent for determining the presence of absence of the concurrent infection in the subject. In some embodiments, the second instructions comprise instructions for determining the body temperature of the subject. In other embodiments, the second reagents comprise reagents for the detection of a bacterial infection in the subject. In still further embodiments, the second reagents comprise reagents for the detection of a viral infection in the subject. In some embodiments, the instructions further comprise instructions for using the kit for diagnosing tubular interstitial disease. In other embodiments, the instructions further comprise instructions for using the kit for predicting the risk of renal tubular injury.

DEFINITIONS

To facilitate an understanding of the present invention, a number of terms and phrases are defined below:

As used herein, the term "surgical procedure" refers to any procedure that involves treament of injury, deformity, or disease by manual or instrumental means.

As used herein, the term "fluorescently activated cell sorting assay" (FACS) refers to any assay suitable for use in cell sorting techniques (e.g., flow cytometry) that employs detection of fluorescent signals.

As used herein, the terms "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular diagnostic test or treatment. Typically, the terms "subject" and "patient" are used interchangeably herein in reference to a human subject.

As used herein, in some embodiments "chemokines" are CXCR3 chemokines, including, but not limited to, IP-10, Mig, and I-TAC. In other embodiments, "chemokines" are CCL class chemokines, which bind to the CCR-5 receptor. Exemplary CCL class chemokines include, but are not limited to, MIP-1α, MIP-3α, and MIP-1β.

As used herein, the term "acute renal failure" refers to an abrupt and sustained decrease in glomerular filtration, urine output, or both. For example, acute renal failure may be an abrupt (1–7 days) and sustained (greater than 24 hours) change from baseline glomerular filtration rate, urine output, or both.

As used herein, the term "predicting acute renal failure, renal tubular interstitial disease or glomerulonephritis risk in a subject" refers to determining the risk of a subject manifesting acute renal failure, rental tubular interstial disease or glomerulonephritis. In some embodiments, predicting acute renal failure, renal tubular interstitial disease, renal cancer or glomerulonephritis risk is based on "detecting the amount of a CXCR3 ligand in the urine of a subject" or "detecting the amount of a CCL chemokine in the urine of a subject." As used herein, the terms "detecting the amount of a CXCR3 ligand in the urine of a subject" and "detecting the amount of a CCL chemokines in the urine of a subject" refer to a quantitative or qualitative measure of the amount of a particular CXCR3 or CCL ligand in the urine of a subject. In some embodiments, the detecting utilizes "reagents for detection of a CXCR3 ligand" or "reagent for the detection of a CCL chemokines."

As used herein, the term "reagents for detection of a CXCR3 ligand" refers to reagents specific for the detection of a given CXCR3 ligand (e.g., IP-10, Mig, and I-TAC), for example, in urine of a subject. In some embodiments, the reagent is an antibody specific for the CXCR3 ligand. In some embodiments, the reagents further comprise additional reagents for performing detection assays, including, but not limited to, controls, buffers, etc.

As used herein, the term "reagents for detection of a CCL chemokine" refers to reagents specific for the detection of a given CCL chemokine (e.g., MIP-1α, MIP-3α, and MIP-1β), for example, in urine of a subject. In some embodiments, the reagent is an antibody specific for the CCL chemokine. In some embodiments, the reagents further comprise additional reagents for performing detection assays, including, but not limited to, controls, buffers, etc.

As used herein, the terms "instructions for using said kit for detecting acute renal failure, renal tubular interstitial disease or glomerulonephritis in said subject" and "instructions for using said kit for predicting acute renal failure, renal tubular interstitial disease or glomerulonephritis in said subject" include instructions for using the reagents contained in the kit for the detection and prediction of acute renal failure, renal tubular interstitial disease or glomerulonephritis in a sample from a subject. In some embodiments, the instructions further comprise the statement of intended use required by the U.S. Food and Drug Administration (FDA) in labeling in vitro diagnostic products. Information required in an application may include: 1) The in vitro diagnostic product name, including the trade or proprietary name, the common or usual name, and the classification name of the device; 2) The intended use of the product; 3) The establishment registration number, if applicable, of the owner or operator submitting the submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A summary of the safety and effectiveness data upon which the substantial equivalence determination is based; or a statement that the safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

As used herein, the term "determining a treatment course of action" as in "determining a treatment course of action based on said predicting acute renal failure, renal tubular interstitial disease or glomerulonephritis risk" or "determining a treatment course of action based on said diagnosing acute renal failure, renal tubular interstitial disease or glomerulonephritis," refers to the choice of treatment administered to a patient. For example, if a patient is found to be at increased risk of acute renal failure, renal tubular interstitial disease or glomerulonephritis, therapy may be started, increased, or changed from one treatment type (e.g., pharmaceutical agent) to another. Conversely, if a patient is found to be at low risk for acute renal failure, renal tubular injury or glomerulonephritis, therapy may not be administered or levels of therapy may be decreased. In some embodiments, the treatment course of action is "continued monitoring" in which no treatment is administered but the levels of chemokine measured in the patients urine is monitored regularly (e.g., using the diagnostic methods of the present invention).

As used herein, the term "determining the efficacy of said acute renal failure, renal tubular interstitial disease or glomerulonephritis drug based on said detecting" refers to determining if a drug is preventing acute renal failure, renal tubular interstitial disease or glomerulonephritis based on, for example, detecting the level of chemokine in the urine of a patient who manifests signs and symptoms of, or is at risk for acute renal failure, renal tubular injury or glomerulonephritis.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the terms "protein microarray" and "protein chip" refer to protein-detecting molecules immobilized at high density on a substrate, and probed for various biochemical activities. (See, for example: Zhu H and Snyder M, "Protein chip technology", Current Opinion in Chemical Biology 7: 55–63, 2003; Cutler P, "Protein arrays: The current state of the art", Proteomics 3; 3–18, 2003; and MacBeath G, "Protein microarrays and proteomics", Nature Genetics Supplement 32: 526–532, 2002, each of which is incorporated herein by reference in its entirety).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., renal acute renal failure, renal tubular interstitial disease, renal cancer or glomerulonephritis). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include urine and blood products, such as plasma, serum and the like. Such examples are not however to be construed as limiting the sample types applicable to the present invention.

DETAILED DESCRIPTION OF THE INVENTION

The present invention provides systems and methods for the diagnosis of kidney diseases, including acute renal failure, renal tubular interstitial disease, renal cancer or glomerulonephritis. In particular, the present invention provides methods of predicting and diagnosing kidney disease based on the presence of chemokines in bodily fluids (e.g., urine). The present invention further provides methods of screening candidate drugs for their efficacy in preventing, treating, and monitoring kidney diseases.

For example, the present invention provides a novel, non-invasive method of correlating the presence of certain chemokines in urine with acute renal failure, renal tubular interstitial disease, renal cancer or glomerulonephritis. The methods are a significant improvement in terms of decreased cost and physical trauma to a patient. The methods of the present invention provide the further advantage of allowing home testing by patients.

I. Detection of Chemokines in Urine

In some embodiments, the present invention provides methods of predicting and diagnosing acute renal failure, renal tubular interstitial disease, renal cancer or glomerulonephritis by detecting chemokines in urine. The present invention is not limited to a particular detection assay. The description below provides non-limiting examples of suitable chemokines and detection methods. The present invention further provides kits for use in detecting chemokines in urine.

A. Urinary Chemokines

The present invention provides methods of detecting chemokines in urine. The urinary chemokines of the present invention are correlated with acute renal failure, renal tubular interstitial disease, renal cancer or glomerulonephritis. In some embodiments, the presence of the peptides or an increased amount of the peptides is indicative of tubular injury. In other embodiments, increased urinary chemokines are correlated with increased risk of acute renal failure, renal interstitial disease, renal cancer or glomerulonephritis. In preferred embodiments, the amount of urinary chemokine is quantitated. In some preferred embodiments, a quantitative level of urinary chemokine is determined that is indicative of an increased risk of acute renal failure, renal tubular interstitial disease, renal cancer or glomerulonephritis. In other embodiments, the level of chemokine is correlated with a functioning level of a drug (e.g., the correct amount or a functional drug).

In preferred embodiments, the chemokines are CXCR3 chemokines. CXCR3 chemokines include, but are not limited to, IL-10, Mig, and I-TAC. In other embodiments, the chemokines are CCL chemokines. CCL chemokines bind to the CCR-5 receptor and include, but are not limited to, MIP-1$\alpha$, MIP-3$\alpha$, and MIP-1$\beta$.

In some embodiments, two or more (e.g., 3 or more, 4 or more, etc.) chemokines are detected to provide a risk assessment. The presence of each marker may provide a more definitive answer than the analysis of any single marker alone. For example, as described in Example 2 below, detection of both IP-10 and I-TAC provided a 100% correlation to renal failure in the patient group tested.

In some embodiments, certain threshold levels of a particular marker are detected. If the threshold level is reached, risk of acute renal failure, tubular interstitial disease, renal cancer or glomerulonephritis is observed. For example, if 100 pg/ml of the rejection marker (e.g., IP-10, I-TAC) in urine is observed, risk is observed. The present invention is not limited by the threshold level used in the analysis. In some embodiments, the threshold level is 20 pg/ml or more, more preferably, 50 pg/ml or more, and most preferably 100 pg/ml or more, although both higher and lower threshold values are contemplated, as are intervals between these values.

B. Detection Methods

The present invention provides methods for detecting the presence of chemokines in a urine sample. In some embodiments, full-length chemokine polypeptide is detected. In other embodiments, a fragment or a portion of chemokine polypeptide is detected. In preferred embodiments, the present invention additionally provides methods of quantifying the amount of a chemokine in urine. The present invention is not limited to a particular detection assay. Exemplary detection assays are described herein.

In some embodiments, chemokines are detected by binding of an antibody specific for the protein (i.e., an immunoassay). The present invention is not limited to a particular antibody. Any antibody (e.g., monoclonal or polyclonal) that detects chemokines may be utilized. Exemplary methods for the generation of antibodies are described below.

Antibody binding is detected by techniques known in the art. For example, in some embodiments, antibody binding is detected using a suitable technique, including but not limited to, radio-immunoassay, ELISA (enzyme-linked immunosorbant assay), "sandwich" immunoassay, immunoradiometric assay, gel diffusion precipitation reaction, immunodiffusion assay, precipitation reaction, agglutination assay (e.g., gel agglutination assay, hemagglutination assay, etc.), complement fixation assay, immunofluorescence assay, protein A assay, and immunoelectrophoresis assay.

In some preferred embodiments, a quantitative ELISA assay is utilized (See e.g., U.S. Pat. Nos. 5,958,715, and 5,484,707, each of which is herein incorporated by reference). In some preferred embodiments, the quantitative ELISA is a competitive ELISA. In a competitive ELISA, the wells of a microtiter plate are first coated with a fusion protein comprising all or a fragment of the chemokine (e.g., a CXCR3 or CCL ligand). The sample to be tested is added to the plate along with an antibody that is specific for the chemokine. The chemokine in the urine sample competes for binding to the antibody with the immobilized peptide. The plate is washed and the antibody bound to the immobilized chemokine polypeptide is then detected using any suitable method (e.g., a secondary antibody comprising a label or a group reactive with an enzymatic detection system). The amount of signal is inversely proportional to the amount of chemokine polypeptide present in the urine sample (e.g., a high signal is indicative of low amounts of chemokine polypeptide being present in the urine).

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the level of chemokine polypeptide in the urine is utilized. In other embodiments, the immunoassay described in U.S. Pat. Nos. 5,789,261, 5,599,677 and 5,672,480, each of which is herein incorporated by reference, is utilized.

In still other embodiments, a protein microarray or protein chip array assay is utilized for detection (See e.g., U.S. Pat. No. 6,197,599, herein incorporated by reference). In such an assay, proteins (e.g., antibodies specific for a chemokine polypeptide) are immobilized on a solid support such as a chip. A urine sample suspected of containing the chemokine polypeptide is passed over the solid support. Bound chemokine polypeptides are then detected using any suitable method. In some embodiments, detection is via surface plasmon resonance (SPR) (See e.g., WO 90/05305, herein incorporated by reference). In SPR, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical or chemical substance. The organic film contains antibodies (e.g., specific for a chemokine polypeptide of the present invention), which can bind with an analyte (e.g., chemokine) in a sample to cause an increased thickness, which shifts the SPR angle. By either monitoring the position of the SPR angle, or the reflectivity at a fixed angle near the SPR angle, the presence or absence of an analyte in the sample can be detected.

In other embodiments, The PROTEINCHIP (Ciphergen Biosystems, Fremont, Calif.) is utilized for detection. The PROTEINCHIP system uses SELDI (Surface-Enhanced Laser Desorption/Ionization) technology to perform the separation, detection and analysis of proteins at the femtomole level directly from biological samples (See e.g., U.S. Pat. No. 6,294,790 and U.S. patent application US 20010014461A1, each of which is herein incorporated by reference. In the PROTEINCHIP technology, proteins of interest (e.g., chemokine polypeptides) are captured on the PROTEINCHIP Array (e.g., via a bound antibody) directly from the original source material. The chip is washed to remove undesired materials and bound proteins are detected using SELDI.

In some embodiments, a cytometric bead array assay is used (Quantum Plex kit, Bangs Laboratories; Cytometric Bead Array kit, BD Biosciences). These systems allow for multiple analyte detection with small volume samples. In other emobidments, a Luminex bead assay is used.

The present invention is not limited to the detection of chemokines in urine. Any bodily fluid that contains elevated levels of chemokine correlated with acute renal failure, renal tubular interstitial injury, renal cancer or glomerulonephritis may be utilized, including, but not limited to, blood, serum, lymph, and saliva.

Figure 1:
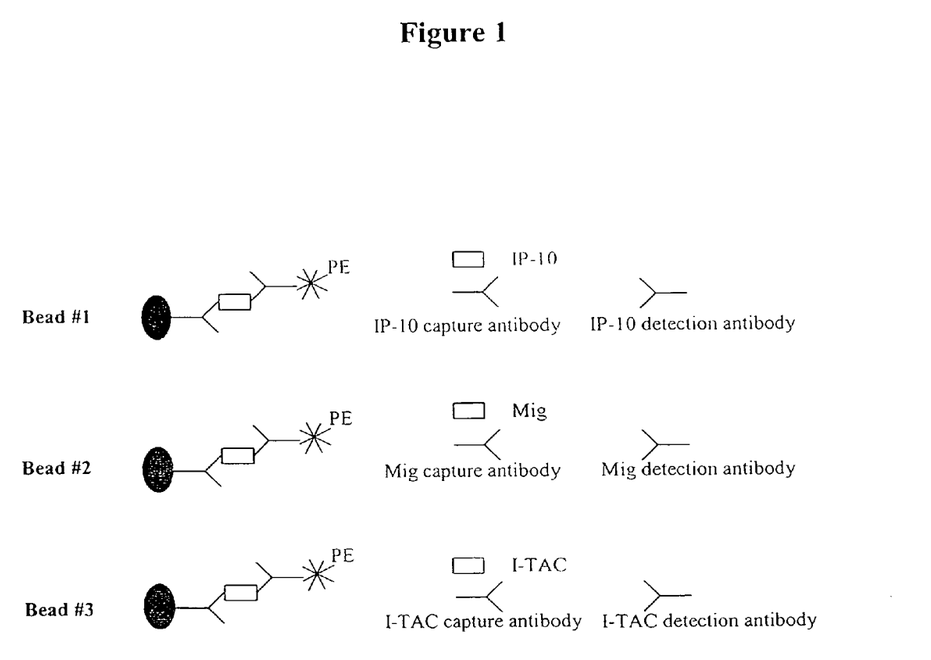
FIG. 1 shows the design of the Beads FACS method for quantification of chemokines IP-10, Mig, and I-TAC used in some embodiments of the present invention.

In some particularly preferred embodiments, a combination of several chemokines are detected simultaneously in urine samples. In some embodiments, the present invention provides a fluorescently activated cell sorting (FACS) method for the simultaneous detection of multiple chemokines. In some embodiments, the method uses fluorescence dye labeled beads that can detect multiple (e.g., at least 3) chemokines in one assay. In one exemplary embodiment (Example 3), the assay was used to detect IP-10, I-TAC and Mig. Detection of these three chemokines was conducted in the same test tube simultaneously as depicted in FIG. 1. As the chemokine concentration increases, the mean fluorescence intensity for each group of beads increases. This correlation between the chemokine concentration and the mean fluorescence establishes the basis for this FACS quantitative method. A standard curve for each chemokine was constructed. These results demonstrate a quantitative assay for the simultaneous detection of multiple chemokines.

The present invention is further not limited to the direct detection of chemokine polypeptides. The present invention contemplates the detection of correlated polypeptides or compounds (e.g., chemokine mRNA, metabolites, etc.). In still further embodiments, the present invention provides methods of detecting the interaction of chemokines with cheomkine receptors (e.g., CXCR3 or CCR-5 receptors).

C. Detection of Concurrent Infection

In some embodiments, assays for the detection of chemokines are combined with assays for the detection of concurrent infections (e.g., bacterial or viral infections) that may generate false-positive results. For example, infection may cause elevated levels of chemokines. In some embodiments, the presence of infection is monitored along with the presence of chemokines.

In some embodiments, infection is monitored by the presence of diagnostic symptoms (e.g., including, but not limited to, elevated body temperature, swelling or redness, and pain). In other embodiments, infection is monitored by monitoring the presence of infectious organisms such a bacteria, virus, or fungus. In still further embodiments, infection is monitored by monitoring the presence of elevated chemokines that are associated with infection, but not acute renal failure, renal tubular interstitial disease, renal cancer or glomerulonephritis. In yet other embodiments, infection is monitored by an elevated white blood cell count in a subject.

D. Kits

In some embodiments, the present invention provides kits for the detection of chemokines. In some embodiments, the kits contain antibodies specific for chemokines in addition to detection reagents and buffers. In some embodiments, the kits contain reagents and/or instructions for testing for concurrent infections. In preferred embodiments, the kits contain all of the components necessary to perform a detection assay, including all controls, directions for performing assays, and any necessary software for analysis and presentation of results.

In some embodiments, the kits contain an assay in a test strip format. In such embodiments, the detection reagent (e.g., antibody), as well as any control or secondary antibodies, are affixed to a solid support. In some embodiments, the solid support is a test strip suitable for dipping into a solution of urine (See e.g., U.S. Pat. Nos. 6,352,862, 6,319, 676, 6,277,650, 6,258,548, and 6,248,596, each of which is herein incorporated by reference).

In some embodiments, the kits are marketed as in vitro diagnostics. The marketing of such kits in the United States requires approval by the Food and Drug Administration (FDA). The FDA classifies in vitro diagnostic kits as medical devices. The 510(k) regulations specify categories for which information should be included.

II. Patient Care

The present invention further provides methods of providing test kits to patients in a variety of settings. The test kits of the present invention are suitable for use in both clinical and home testing settings. In preferred embodiments, test kits are approved for sale as in vitro diagnostics as described above.

A. Home Testing

In some embodiments, the present invention provides kits for home testing. In preferred embodiments, the kits are approved as in vitro diagnostics for home use under guidelines as described above. Patients may use home test kits to monitor acute renal failure, renal tubular interstitial disease, renal cancer or glomerulonephritis. In some embodiments, test kits for home use are qualitative rather than quantitative. For example, in some embodiments, the test registers a positive result if urine levels of a CXCR3 or CCL ligand are above a pre-determined level (e.g., above approximately 100 pg/mL) or increase over time. In other embodiments, the tests are quantitative (e.g., utilizing the quantitative methods described above).

For example, in some embodiments, patients at risk for acute renal failure, renal tubular interstitial disease or glomerulonephritis monitor urine levels of CXCR3 or CCL ligands. In preferred embodiments, patients conduct serial monitoring (e.g., from once a day to once a month or every several months) to screen for early signs or renal failure. In preferred embodiments, patients whose urine level of a CXCR3 or CCL ligand is above a pre-determined level (or register a positive result in a quantitative assay) are instructed to seek medical advice.

In other embodiments, the test kits are utilized by patients at home to monitor the effectiveness of a drug. For example, in some embodiments, a patient who is taking a drug following acute renal failure, renal tubular disease, renal cancer or glomerulonephritis monitors levels of a CXCR3 and/or CCL ligand on a regular basis (e.g., from once a day to once a month or every several months). If a patient's level of a CXCR3 or CCL ligand is above a pre-determined level (or registers a positive result in a quantitative assay), it may be indicative of organ failure caused by lack of an effective level of a drug. Such patients are advised to schedule a follow up with a caregiver (e.g., to adjust the medication levels, or switch to a different drug).

B. Clinical-Based Testing

In other embodiments, testing is performed in a clinical (e.g., hospital or clinic) setting. In such embodiments, testing is generally ordered and interpreted by a physician or other clinician. In some embodiments, testing is carried out by a lab technician (e.g., in an in-house or external clinical lab). In preferred embodiments, clinical testing utilizes a quantitative assay for detection of a CXCR3 or CCL ligand. In some embodiments, testing is utilized to determine the likelihood of organ failure in a patient with acute renal failure, renal tubular interstitial disease or glomerulonephritis. In other embodiments, testing is utilized to monitor organ function in a subject who has recovered from acute renal failure, renal tubular interstitial disease or glomerulonephritis, and is not on medication. In still further embodiments, testing is utilized to monitor the effectiveness of a medication. In some embodiments, the urinary chemokine test is used to complement allograft biopsy and serum Cr, and to monitor response to therapy. In a preferred embodiment, the urinary chemokine test is used as a reference parameter in deciding whether and when a biopsy should be taken. Combining serum Cr with the urinary chemokine test distinguishes acute dysfunction of the renal allograft, which is medical emergency and needs urgent treatment, from non-acute elevations of serum creatinine (Cr) and dysfunction. For patients with elevated Cr and urinary IP-10/Mig, a biopsy should be immediately taken and an accurate diagnosis should be made before the initiation of therapy. In another embodiment, in patients who have concurrent elevation of serum Cr and urinary chemokines, if a BK virus test on urinary cells either by microscopic observation or polymerase chain reaction is also positive, the likelihood of BK virus nephritis is very high, and a biopsy may be avoided. In a further embodiment, if the serum Cr is increased, but there is a normal level of urinary chemokines, elevation of serum Cr may be due to chronic insidious damage to the renal graft. In this circumstance, a biopsy is delayed or even avoided. In still further embodiments, urine chemokine levels are useful in patients whose biopsy reveals borderline rejection in assessing the need for anti-rejection therapy. In yet further embodiments, the urine chemokine test distinguishes active low-grade damage in patients having dormant infiltrating immune cells as found in many biopsies from renal grafts reveal numerous infiltrating immune cells. These patients often have a normal serum Cr. In additional embodiments, the urinary chemokine test is used as an early index of the response to anti-rejection therapy. In particularly preferred embodiments, the urinary IP-10 test is useful in recipients with acute rejection that is superimposed on chronic injury causing an elevated baseline of serum Cr. In these patients serum Cr may not return to the baseline level, but the urinary IP-10 will decline as acute injury resolves.

The urinary chemokine test of the present invention is simple to conduct and rapid, making it suitable for clinical use. In some embodiments, testing is utilized as a follow up to home testing by a patient (e.g., when a CXCR3 or CCL ligand level is elevated or the patient has other clinical symptoms of acute renal failure, renal tubular disease or glomerulonephritis). Based on the result of the clinical testing, the appropriate intervention is taken (e.g., including, but not limited to, an increase or decrease in levels of drug therapy, initiation of drug therapy, termination of therapy, or continued monitoring).

C. Home Collection/Clinic Testing

In still further embodiments, testing is provided by a clinical lab but in the absence of a physician's order or interpretation. For example, in some embodiments, the patient collects a urine specimen and transports the specimen to a clinical lab (e.g., by mail or in person). The clinical lab then reports the result to the patient. In other embodiments, the patient provides a sample at a clinical lab, the sample is analyzed, and the results are returned to the patient. The patient then decides, based on the level of CXCR3 or CCL ligand in the urine (or the presence or absence of a positive result in a qualitative assay) whether or not to contact a physician for follow up care.

III. Antibodies

The present invention provides isolated antibodies. In preferred embodiments, the present invention provides monoclonal antibodies that specifically bind to an isolated polypeptide comprised of at least five amino acid residues of a CXCR3 or CCL ligand. These antibodies find use in the diagnostic methods described herein. In other embodiments, commercially available antibodies are utilized (e.g., available from any suitable source including, but not limited to, R & D System, Minneapolis, Minn.).

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495[1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a CXCR3 or CCL ligand). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a CXCR3 or CCL ligand) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared, and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide-activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a CXCR3 or CCL ligand polypeptide (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

IV. Drug Screening

In some embodiments, the present invention provides drug-screening assays (e.g., to screen for effective acute renal failure, renal tubular interstitial disease or glomerulonephritis drugs). The screening methods of the present invention utilize the detection of a CXCR3 ligand. For example, in some embodiments, the present invention provides methods of screening for compounds that alter (e.g., increase or decrease) the expression of CXCR3 or CCL ligand. In some embodiments, the level of a CXCR3 or CCL ligand is detected (e.g., using a method described herein) in a subject that has undergone administration of a candidate compound. The increased level of a CXCR3 or CCL ligand is indicative of a candidate compound that is not preventing renal failure. Conversely, preferred candidate compounds are those that prevent the elevation of CXCR3 or CCL ligand levels.

In some embodiments, drug screening assays are performed in animals. Any suitable animal may be used including, but not limited to, baboons, rhesus or other monkeys, mice, or rats. Animal models of acute renal failure, renal tubular interstitial disease, renal cancer or glomerulonephritis are generated (e.g., by the administration of compounds that trigger renal failure), and the effect of candidate drugs on the animals is measured. In preferred embodiments, acute renal failure, renal tubular interstitial disease, renal cancer or glomerulonephritis in the animals is measured by detecting levels of chemokines in the urine of the animals. The level of chemokines may be detected using any suitable method, including, but not limited to, those disclosed herein.

Experimental

The following examples are provided in order to demonstrate and further illustrate certain preferred embodiments and aspects of the present invention, and are not to be construed as limiting the scope thereof.

EXAMPLE 1

Correlation of Urine IP-10 with Graft Rejection

This example describes the correlation of urine levels of IP-10 with kidney graft rejection in human subjects. Forty-five human subjects that had undergone kidney transplant were investigated. Urine IP-10 levels were measured serially after organ transplantation. IP-10 levels were measured using a quantitative calorimetric sandwich ELISA assay (R & D Systems, Minneapolis, Minn.). Subjects were divided into two groups, rejecters and non-rejecters, based on kidney biopsies. Biopsies were classified using Banff criteria. All subjects were receiving anti-rejection therapy at the time of the study. Urine from ten normal (non-transplant) subjects was also tested.

In a majority of the non-rejecters, IP-10 levels remained at a constant, low level or decreased over time. In the rejecters, IP-10 levels remained at a constant, high level or increased over time. A urine level of IP-10 of greater than approximately 100 pg/mL was associated with organ rejection. There was no detectable IP-10 in any of the normal control samples. This Example demonstrates that IP-10 levels are correlated with kidney transplant rejection.

Experiments conducted during the development of the present invention also demonstrated a correlation between CCL chemokines and rejection. For example, correlations were observed for the CCL chemokines MIP-1α, MIP-3α, and MIP-1 β.

EXAMPLE 2

Correlation of Urinary Chemokines with Graft Rejection and Treatment

This example describes the correlation of urinary chemokines levels with graft rejection and treatment. Urinary samples were collected from healthy individuals, kidney transplant recipients with stable graft function, and recipients with acute rejection. All patients with acute rejection were hospitalized and received anti-rejection therapy. Urinary samples were centrifuged, and supernatant was aliquoted and stored at −80° C. These samples, after thawing, were evaluated by ELISA for the expression of MCP-1, IP-10, and I-TAC.

Elevated Expression of Chemokines in Urinary Samples from Patients with Acute Rejection As shown in Table 1, chemokines IP-10 and I-TAC were significantly increased in the urinary samples of patients with acute graft rejection and acute tubular injury, compared to healthy controls and kidney transplant patients with other pathologic changes. As presented in Table 2, if 100 pg/ml was used as the cut-off level and IP-10 and I-TAC were considered simultaneously, 80% of samples from patients with rejection and acute tubular injury were above this level, but less than 5% of the patients in the remaining groups were above this level. This result indicates that detection of IP-10 and I-TAC in the urinary samples reflects the acute rejection/acute tubular injury in the kidney grafts.

MCP-1 was also examined in the urinary samples. In the present series of samples (Table 1), urinary MCP-1 was increased in patients with acute rejection or acute tubular injury. However, the difference of MCP-1 levels between acute rejection/acute tubular injury and the remaining groups of patients was not significant.

TABLE 1

Urinary Chemokine Levels in Patients with Kidney Transplant

|  | Healthy Controls (n = 10) | Others (non-acute/Chronic Rejection; n = 16) | Chronic Rejection (n = 7) | Acute Tubular Injury (n = 3) | Suspicious Acute Rejection (n = 7) | Acute Rejection (n = 10) Day 1/Day 2* |
|---|---|---|---|---|---|---|
| IP-10 (pg/ml) | 1 | 12 | 31 | 362 | 27.8 | 376/579 |
| I-TAC (pg/ml) | 1 | 21 | 13 | 75 | 44 | 94.2/168 |
| MCP-1 (pg/ml) | 269 | 641 | 1908 | 3226 | 528 | 2060/2473 |

*Day 1/Day 2 indicates the biopsy day/the day after the biopsy day.

TABLE 2

Patients with Urinary IP-10 and I-TAC Levels above 100 pg/ml

|  | Healthy Controls (n = 10) | Others (nonacute/Chronic Rejection; n = 16) | Chronic Rejection (n = 7) | Acute Tubular Injury (n = 3) | Suspicious Acute Rejection (n = 7) | Acute Rejection (n = 10) Day 1/Day* |
|---|---|---|---|---|---|---|
| IP-10 | 0 | 0 | 0 | 3 | 1 | 7/6 |
| I-TAC | 0 | 0 | 0 | 1 | 0 | 4/6 |
| IP-10 or I-TAC | 0 | 0 | 0 | 3 | 1 | 8/8 |

*Day 1/Day 2 indicates the biopsy day/the day after the biopsy day.

Return of Urinary Chemokine Levels to Baseline after Resolution of Acute Rejection Urinary samples were collected daily from patients with biopsy-proven acute graft rejection until the rejection resolved. IP-10 and I-TAC were determined in these samples with ELISA. IP-10 and I-TAC were elevated at the time of diagnosis, but the levels decreased after anti-rejection therapy was started, and finally returned to the baseline. These results indicate that chemokine levels are useful parameters for monitoring the therapeutic response to anti-rejection therapies. In contrast, MCP-1 levels did not return to baseline in at least 50% of the patients with acute rejection following successful treatment. This example indicates that IP-10 and I-TAC levels correlate with acute rejection processes in the kidney graft.

EXAMPLE 3

Flow Cytometry Based Technique for Quantification of Chemokines

This example describes a FACS method for the simultaneous detection of multiple chemokines. The fluorescence activated cell sorting (FACS) method uses fluorescence dye labeled beads that can detect 3 chemokines in one assay. In this example, IP-10, I-TAC and Mig were detected. Detection of the three chemokines was conducted in the same test tube simultaneously as depicted in FIG. 1. As the chemokine concentration increases, the mean fluorescence intensity for each group of beads increases. This correlation between the chemokine concentration and mean fluorescence establishes the basis for the FACS quantitative method. A standard curve for each chemokine was constructed. This example demonstrates that IP-10, Mig and I-TAC can be simultaneously detected in a urinary sample.

EXAMPLE 4

Urinary Chemokine Assay Using the Luminex Microsphere Platform

Subjects

Ninety-nine renal allograft recipients were recruited and donated 350 urinary samples. Among the patients, 28 were diagnosed with acute rejection, 9 with borderline rejection, 6 with BK virus nephritis, 10 with acute tubular injury, 20 with chronic rejection, and 26 with stable graft function without graft injury. Urinary samples were also collected from 16 healthy non-transplanted individuals. Renal transplant recipients with symptoms and elevated serum creatinine (Cr) underwent renal transplant biopsy which was used as the diagnostic standard. Acute and chronic rejection events were scored according to Banff criteria by a renal transplant pathologist. BK virus infection was diagnosed using light microscopy identification of pleomorphic, enlarged tubular epithelial cell nuclei containing characteristic "smudgy" inclusions. The suspicion of BK virus infection was confirmed in all cases by immunohistochemistry using a polyclonal polyoma virus-reactive antibody. Urine samples (50 ml) were collected prior to biopsy by clean catch from the renal transplant recipients who had an elevated Cr of 20% or more above baseline and who were to undergo renal transplant biopsy as a diagnostic procedure. Patients with biopsy proven acute rejection were hospitalized, treated with anti-rejection therapy, and donated daily urinary samples until the rejection resolved. The collected samples were centrifuged at 1500 rpm for 10 min. The supernatant of each sample was aliquoted and stored at −80° C. until use. At the time of experiments, samples were thawed and evaluated for the levels of IP-10, Mig and I-TAC.

Quantification of Urinary IP-10, Mig and I-TAC

Luminex (Austin, Tex.) Multi-Analyte Profiling (xMAP) Technology and Renovar (Madison, Wis.) human CXCR3 binding chemokines triplex assay kits were used for quantification of urinary IP-10, Mig and I-TAC. Luminex xMAP is based on polystyrene particles (microspheres) that are internally labeled with 2 different fluorophores. When excited by a 635-nm laser, the fluorophores emit light at different wavelengths, 658 and 712 nm. By varying the 658-nm/712-nm emission ratios, the beads are individually classified by the unique Luminex 100 IS analyzer. A third fluorophore coupled to a reporter molecule allows for quantification of the interaction that has occurred on the microsphere surface. The capture antibodies directed respectively to IP-10, Mig and I-TAC were separately pre-conjugated to their corresponding particles following the Luminex coupling protocol. The quantification of CXCR3 binding chemokines was conducted in 96-well flat-bottom plates. Twenty-five µl of mixed IP-10, Mig and I-TAC standards or urinary samples were added to wells containing 25 µl of assay buffer and 25 µl of pre-coated particles, and incubated on a 3-D rotator (Labline Instrument Inc., Melrose Park, Ill.) at 60 rounds/min at room temperature (RT) for 60 min. Mixed biotin labeled detection antibodies directed at IP-10 (BD PharMingen, San Jose, Calif.), Mig and I-TAC (R&D Systems, Minneapolis, Minn.) were then added and incubated on the rotator at 60 rounds/min at RT for 60 min before the addition of streptavidin-PE (BD PharMingen). After an additional 30 min incubation on the rotator at 60 rounds/min at RT, data acquisition and analysis were performed on a Luminex 100 IS analyzer.

Statistical Analysis

The levels of urinary IP-10, Mig and I-TAC were expressed as mean value±standard error (SE). The statistical significance of the findings was assessed by ANOVA using computer software Prism 4 from GraphPad Software (San Diego, Calif.), and a p value less than 0.05 was considered significant. The urinary chemokine threshold that gave the maximal sensitivity and specificity for the diagnosis of acute dysfunction of renal allograft was 100 pg/ml. Sensitivity, specificity, positive predictive value (PPV) and negative predictive value (NPV) of the urinary chemokine test was calculated as follows: sensitivity=number of true positive specimens (TP)/[TP+number of false negative specimens (FN)]; specificity=number of true negative specimens (TN)/[TN+number of false positive specimens (FP)]; PPV=TP/(TP+FP), and NPV=TN/(TN+FN).

Levels of Urinary Chemokines in Patients and Control Individuals

Figure 2:
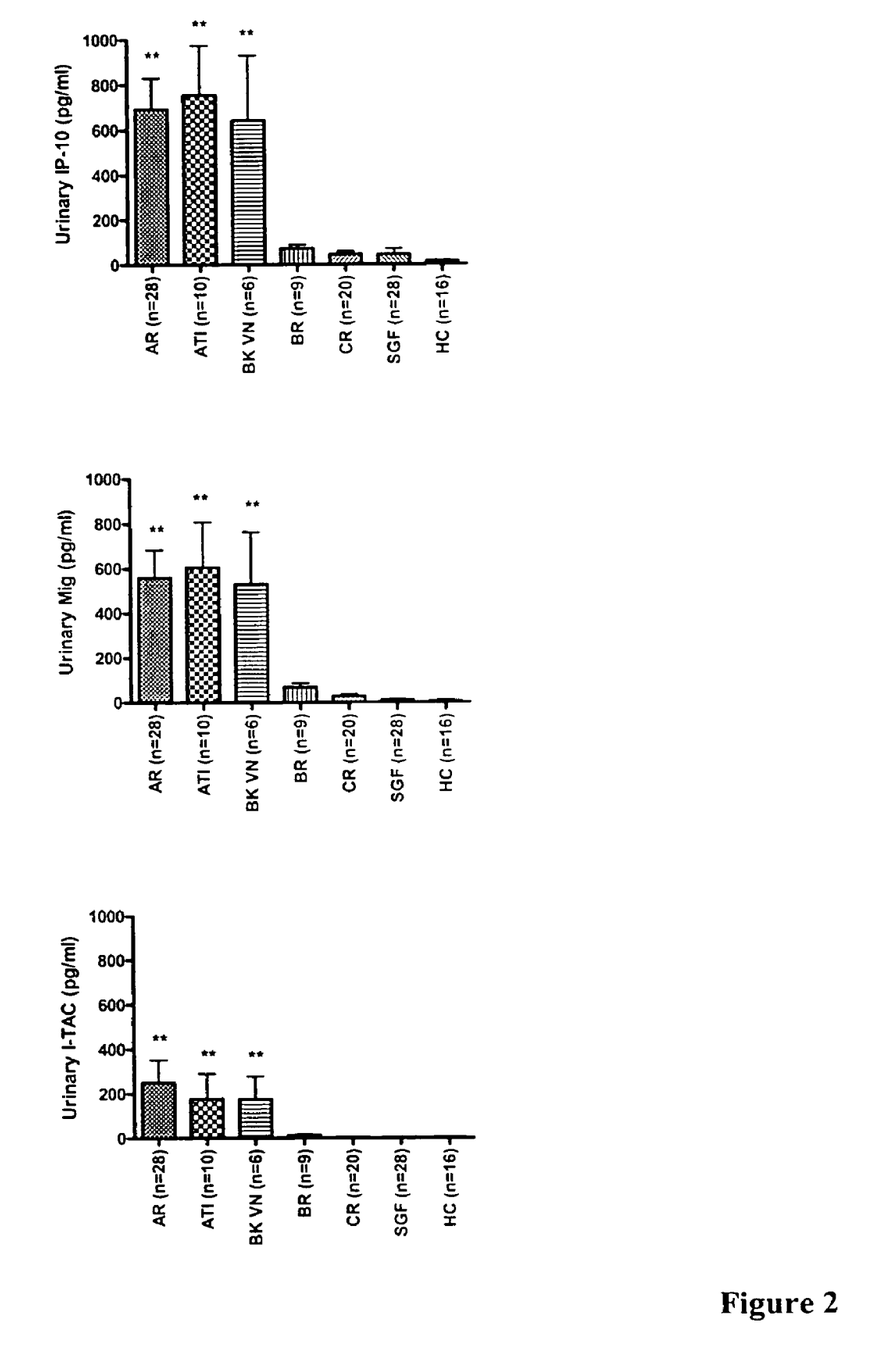
FIG. 2 shows urinary levels of CXCR3 binding chemokines IP-10, Mig and I-TAC in recipients of renal allografts, acute tubular injury, BK virus nephritis, borderline rejection, chronic rejection, stable graft function and healthy controls.

Urinary IP-10, Mig and I-TAC were simultaneously quantified in each urine sample by the Luminex xMAP method. FIG. 2 shows that urinary levels of CXCR3-binding chemokines IP-10, Mig and I-TAC were significantly elevated (P<0.01) in samples collected from recipients with acute rejection (AR), BK virus nephritis (BK VN), and acute tubular injury (ATI), but not in samples collected from recipients with borderline rejection (BR), chronic rejection (CR), and stable graft function (SGF). Furthermore, urinary samples collected from healthy control (HC) individuals contained very low levels of the measured chemokines (FIG. 2).

Figure 3:
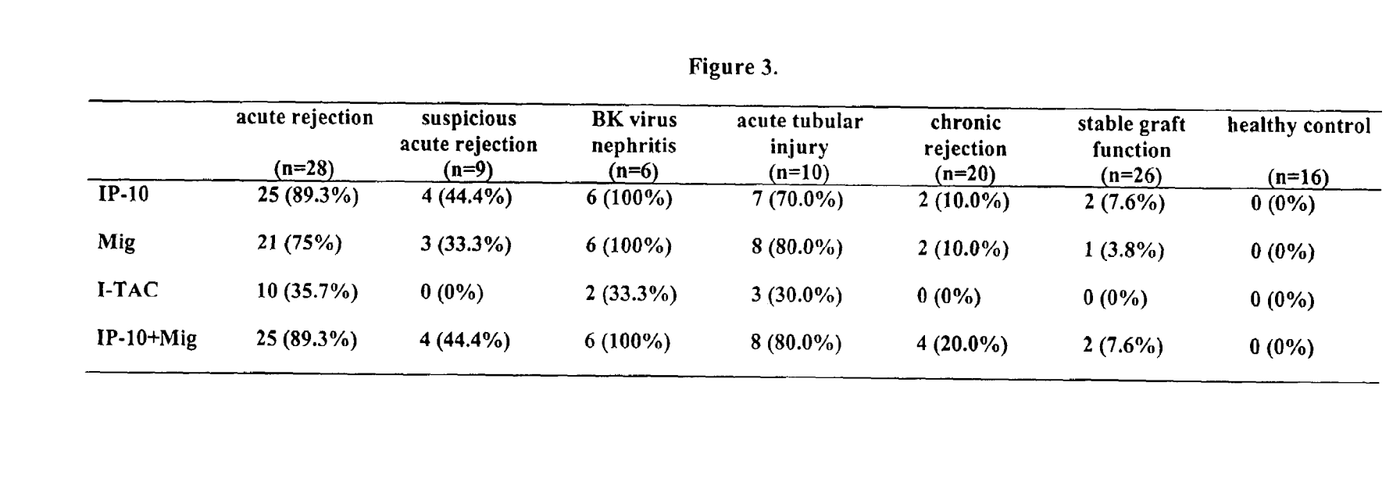
FIG. 3 shows a comparison of kidney graft recipients with acute rejection, borderline rejection, BK virus nephritis, acute tubular injury, chronic rejection stable graft function and healthy controls with urinary chemokine levels greater than 100 pg/mL.
Figure 4:
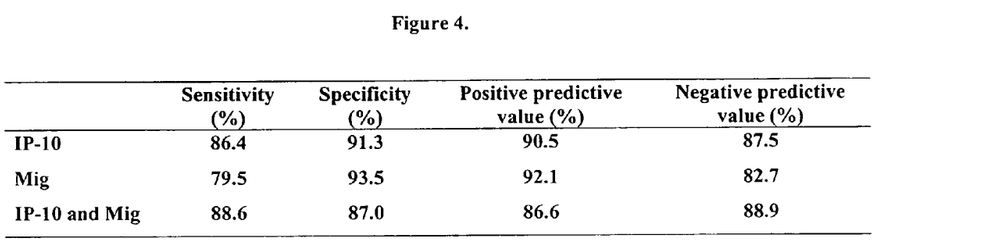
FIG. 4 shows values of IP-10/Mig in differentiation of recipients with acute dysfunction (for example, acute rejection, acute tubular injury and BK virus nephritis) from recipients with chronic rejection and stable graft function.

Urinary Chemokines as a Sensitive and Specific Indicator of Acute Renal Allograft Dysfunction After renal transplantation, graft dysfunction may occur due to treatable etiologies such as acute rejection, acute tubular injury, or BK virus nephritis. Other types of graft injury may occur more insidiously and usually do not require acute intervention, such as chronic rejection and recurrence of the original disease. Acute dysfunction refers herein to acute rejection, acute tubular injury and BK virus nephritis. Levels of urinary IP-10, Mig and I-TAC varied greatly among the study subjects, ranging from 0 pg/ml to 2000 pg/ml. Using 100 pg/ml as the cutoff level for the urinary chemokines that gave the maximal sensitivity and specificity, as presented in FIG. 3, most of the renal graft recipients with acute rejection, BK virus nephritis and acute tubular injury had higher levels of urinary IP-10 and Mig, while most of the recipients with chronic rejection and stable graft function had lower levels of urinary IP-10 and Mig (FIG. 3). For recipients with borderline rejection, 4 out of 9 cases showed higher levels. None of the healthy controls had urinary IP-10, Mig or I-TAC higher than 100 pg/ml. The elevation of urinary IP-10 and Mig was more prevalent than I-TAC in recipients with acute dysfunction caused by acute rejection, acute tubular injury and BK virus nephritis. As shown in FIG. 2 and FIG. 3, elevation of urinary IP-10 and Mig indicated acute renal injury by one of the three etiologies. To evaluate the value of urinary IP-10 and/or Mig to differentiate the acute dysfunction from chronic rejection and stable graft function, we calculated the sensitivity, specificity, positive predictive value and negative predictive value as presented in FIG. 4. Both IP-10 and Mig are highly sensitive and specific.

Urinary chemokine levels were compared to the renal function indicator, serum Cr. When urinary IP-10 was used in the analysis, most of the recipients with acute dysfunction had increased urinary IP-10 and serum Cr. Recipients with chronic rejection had increased Cr, but not IP-10. Recipients with stable graft function had low IP-10 and Cr levels.

Decline of Urinary Chemokines after Anti-Rejection Therapy

Figure 5:
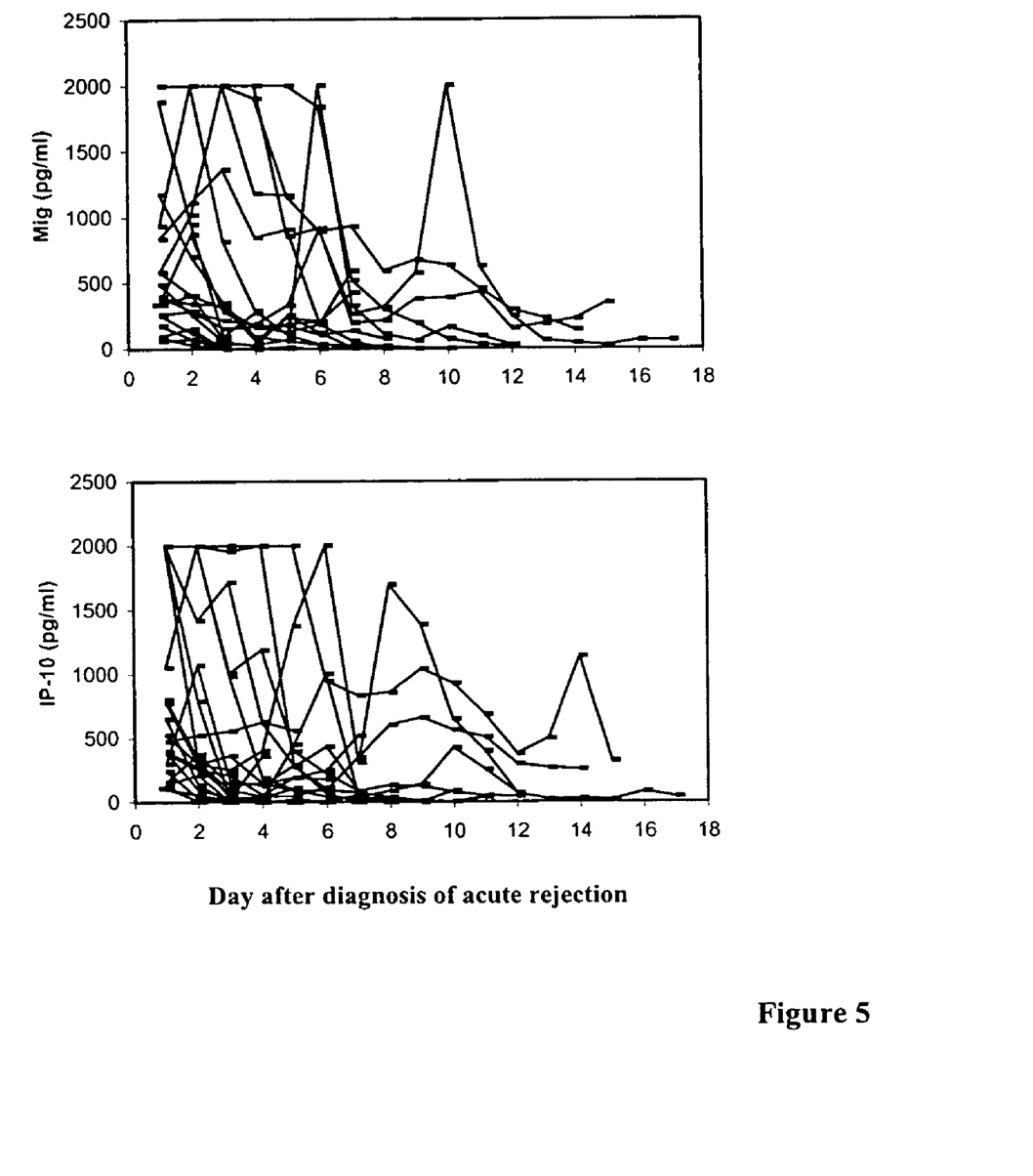
FIG. 5 shows the decline of urinary IP-10 and Mig in recipients with acute rejection after anti-rejection therapy.

Among the 28 patients with acute rejection, daily urinary samples were collected from 24 during hospitalization for anti-rejection therapy. Day 1 is the time that acute rejection was diagnosed and anti-rejection therapy was initiated. As presented in FIG. 5, urinary IP-10 and Mig declined with the initiation of anti-rejection therapy on day 1, and most of the recipients reached a level below 100 pg/ml in their last collected urinary sample.

Figure 6:
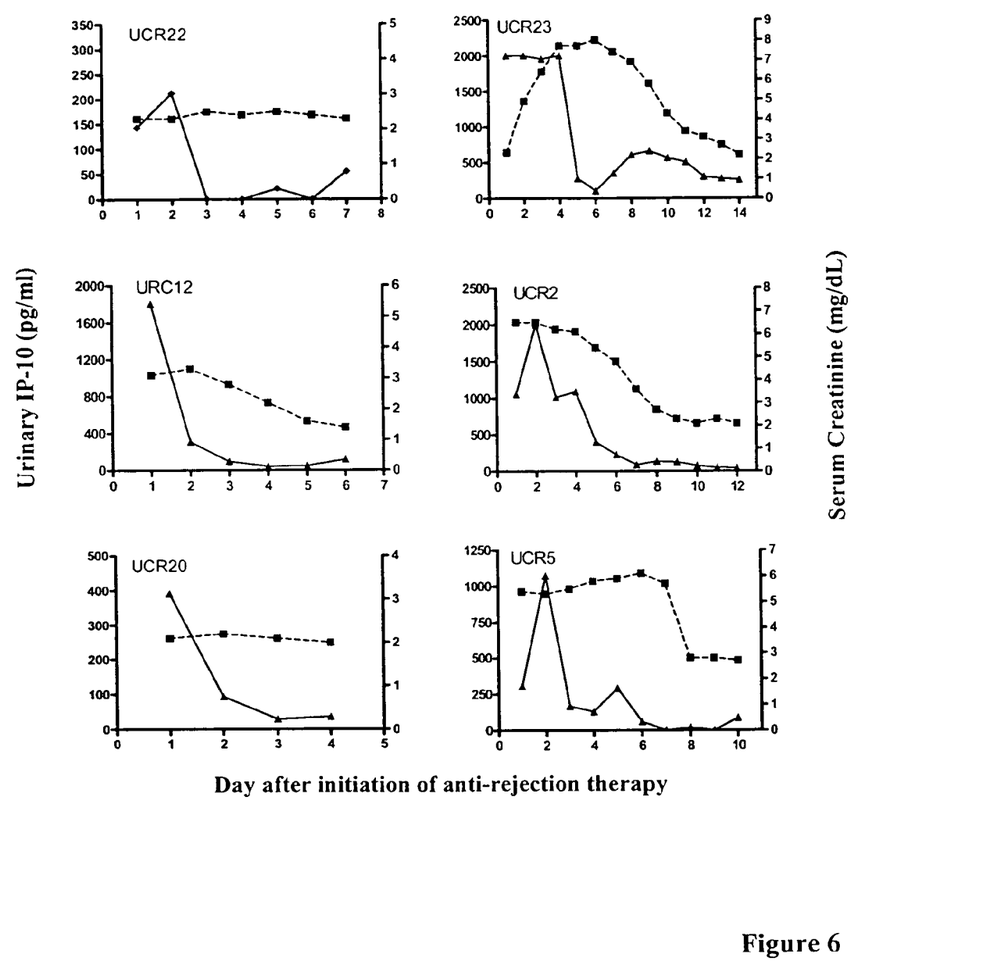
FIG. 6 shows that urinary IP-10 levels decline several days earlier than serum creatinine in acute rejection patients receiving anti-rejection therapy.

Serum Cr is an important parameter used to judge the effectiveness of anti-rejection therapy. Therefore, we compared the levels of serum Cr and urinary chemokines in the recipients who received anti-rejection therapy. As shown in FIG. 6, urinary IP-10 (solid triangle) declined several days earlier than serum creatinine (solid square) in acute rejection patients receiving anti-rejection therapy. Urinary and serum samples were collected once daily from each of the patients, and urinary IP-10 and serum Cr were separately determined. UCR2, UCR5, UCR23, and UCR 12 are representative patients that had elevated serum Cr initially which declined with anti-rejection therapy. UCR20 and UCR22 are representative patients that had elevated serum Cr initially, but Cr did not decline with anti-rejection therapy during the hospitalization period. Thus, as shown in FIG. 6, the serum Cr in the recipients who were hospitalized for 3–14 days could be classified into two patterns: started high and remained high for several days before declining (represented by UCR2, UCR5, UCR23, and UCR 12), or started at the lower range of the abnormal level and maintained that level (represented by UCR20 and UCR22) during the hospitalization. In contrast to serum Cr kinetics, urinary IP-10 declined in all patients, with this decrement starting 2–5 days earlier than the serum Cr (FIG. 6).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of determining the risk of acute renal failure, renal tubular interstitial disease or glomerulonephritis, comprising:
   a) providing;
      i) a urine sample from a subject, wherein said subject is suspected of having a kidney disease; and
      ii) reagents for detection of at least one compound from the group consisting of IP-10 and Mig wherein said reagents for detection are affixed to a solid support; and
   b) contacting said urine sample with said reagents;
   c) detecting the presence or absence of said at least one compound from the group consisting of IP-10 and Mig in said urine sample from said contacting said urine sample with said reagents; and
   d) determining the risk of acute renal failure, renal tubular interstitial disease or glomerulonephritis in said subject based on the result of said detecting.

2. The method of claim 1, wherein said detecting the presence of said at least one compound from the group consisting of IP-10 and Mig in said urine sample comprises detecting the amount of said at least one compound from the group consisting of IP-10 and Mig in said urine sample.

3. The method of claim 1, further comprising the step of detecting the presence or absence of I-TAC.

4. The method of claim 1, wherein said reagents comprise reagents for performing an immunoassay.

5. The method of claim 4, wherein said immunoassay is selected from the group consisting of an ELISA, radioimmunoassay, automated immunoassay, cytometric bead assay, and immunoprecipitation assay.

6. The method of claim 1, wherein said reagents comprise reagents for performing a fluorescently activated cell sorting assay.

7. The method of claim 1, further comprising the step of detecting said presence or absence of said at least one compound from the group consisting of IP-10 and Mig in said urine sample and determining a treatment course of action based on said detecting kidney disease.

8. The method of claim 1, further comprising the step of utilizing said urine sample from said subject in further determining the presence or absence of a concurrent infection in said subject.

9. The method of claim 2, wherein said amount of said at least one compound from the group consisting of IP-10 and Mig in said urine sample is at least 20pg/ml.

10. The method of claim 1, wherein said solid support comprises a test strip.

11. The method of claim 1, wherein said detecting comprises detecting the presence or absence of both IP-10 and Mig.

12. A method of diagnosing acute renal failure, renal tubular interstitial disease or glomerulonephritis in a subject, comprising:
   a) providing;
      i) a urine sample from a subject; and
      ii) reagents for detection of at least one compound from the group consisting of IP-10 and Mig wherein said reagents for detection are affixed to a solid support;
   b) contacting said urine sample with said reagents;
   c) detecting the presence or absence of said at least one compound from the group consisting of IP-10 and Mig in said urine sample using said reagents; and
   d) diagnosing acute renal failure, renal tubular interstitial disease or glomerulonephntis in said subject based on the result of said detecting.

13. The method of claim 12, further comprising the step of detecting the presence or absence of I-TAC.

14. The method of claim 12, further comprising the step of detecting the presence or absence of a compound selected from the group consisting of MIP-1α, MIP-3α, and MIP-1β.

15. The method of claim 12, further comprising the step of detecting said presence or absence of said at least one compound from the group consisting of IP-10 and Mig in said urine sample and determining a treatment course of action based on said detecting acute renal failure, renal tubular interstitial disease or glomerulonephritis.

16. The method of claim 12, further comprising the step of utilizing said urine sample from said subject in further determining the presence or absence of a concurrent infection in said subject.

17. The method of claim 12, wherein said detecting the presence or absence of said at least one compound from the group consisting of IP-10 and Mig in said urine sample using said reagents in diagnosing said acute renal failure, renal tubular interstitial disease or glomerulonephritis comprises detecting the amount of said at least one compound from the group consisting of IP-10 and Mig in said urine sample.

18. The method of claim 17, wherein said amount of said at least one compound from the group consisting of IP-10 and Mig in said urine sample is at least 20pg/ml.

19. The method of claim 12, wherein said solid support comprises a test strip.

20. The method of claim 12, wherein said detecting comprises detecting the presence or absence of both IP-10 and Mig.

* * * * *